United States Patent
Khoubyari

(10) Patent No.: US 8,185,426 B1
(45) Date of Patent: May 22, 2012

(54) METHOD AND SYSTEM FOR PROVIDING REAL TIME APPOINTMENT RESCHEDULING

(75) Inventor: Siamak Khoubyari, San Jose, CA (US)

(73) Assignee: Intuit Inc., Mountain View, CA (US)

( * ) Notice: Subject to any disclaimer, the term of this patent is extended or adjusted under 35 U.S.C. 154(b) by 834 days.

(21) Appl. No.: 12/263,676

(22) Filed: Nov. 3, 2008

(51) Int. Cl.
*G06Q 10/00* (2006.01)

(52) U.S. Cl. .......................... 705/7.19; 705/7.16; 705/2

(58) Field of Classification Search ............. 705/2, 7.19, 705/7.16
See application file for complete search history.

(56) References Cited

U.S. PATENT DOCUMENTS

| | | | | |
|---|---|---|---|---|
| 6,343,273 | B1* | 1/2002 | Nahan et al. | 705/5 |
| 6,961,418 | B1* | 11/2005 | Thygeson et al. | 379/210.01 |
| 7,113,797 | B2* | 9/2006 | Kelley et al. | 455/456.2 |
| 7,689,441 | B1* | 3/2010 | Craft | 705/3 |
| 7,809,629 | B2* | 10/2010 | Hustad et al. | 705/37 |
| 7,869,941 | B2* | 1/2011 | Coughlin et al. | 701/533 |
| 8,060,500 | B1* | 11/2011 | Fitch et al. | 707/724 |
| 2002/0184063 | A1* | 12/2002 | Kaufman et al. | 705/7 |
| 2004/0193458 | A1* | 9/2004 | Bear | 705/5 |
| 2006/0068787 | A1* | 3/2006 | Deshpande et al. | 455/435.3 |
| 2006/0147005 | A1* | 7/2006 | Taub | 379/114.2 |
| 2007/0083403 | A1* | 4/2007 | Baldwin et al. | 705/7 |
| 2007/0162308 | A1* | 7/2007 | Peters | 705/2 |
| 2008/0114638 | A1* | 5/2008 | Colliau et al. | 705/9 |
| 2008/0249830 | A1 | 10/2008 | Gilman et al. | |
| 2009/0132329 | A1* | 5/2009 | Lam et al. | 705/9 |

OTHER PUBLICATIONS

Reima Suomi. "Five Finnish innovations in Mobile Government and their root factors." in Collaborative Electronic Commerce Technology and Research, Proceedings 2006.*
TrakCare Solution Guide 2007.*
Fitch, "Method and System for Proactively Filling Appointment Times", U.S. Appl. No. 12/328,889, filed Dec. 5, 2008.

* cited by examiner

*Primary Examiner* — Lynda Jasmin
*Assistant Examiner* — George H Walker, III
(74) *Attorney, Agent, or Firm* — McKay and Hodgson, LLP; Philip McKay; Sean P. Lewis

(57) ABSTRACT

A system and method for providing real-time appointment rescheduling by providing access to one or more computer-based appointment scheduling systems and a virtual open appointment wait-list associated with one or more appointment slots in the scheduling systems. One or more service consumers request to be placed on the wait-list. When an appointment becomes available, wait-list data is searched to find the first consumer that is next on the wait-list and whose wait-list data is consistent with the newly available appointment. The first consumer is then contacted with a designated period of time to respond and accept the appointment. After the designated period of time has passed with no response from the first consumer, the wait-list data is searched again to find the second service consumer that is next on the wait-list. The process is repeated automatically until the newly available appointment is accepted.

26 Claims, 2 Drawing Sheets

METHOD AND SYSTEM FOR PROVIDING REAL TIME APPOINTMENT RESCHEDULING

BACKGROUND

For most healthcare service providers, the key to maximizing efficiency, and income, is to maximize the number of patient appointments for each business day. To this end, most healthcare service providers schedule an optimum number of appointments for any given business day well in advance. In addition, some healthcare service providers leave openings in their schedules to accommodate emergencies and/or breaks/vacations. However, currently, despite considerable advance planning and efforts to maintain an optimal number of appointments each day, healthcare service providers still often find themselves with inefficient, and costly, appointment free "gaps" during the course of the day. These appointment gaps occur for a variety of reasons. One significant source of appointment gaps is that, particularly in the healthcare services industry, there are a large number of patient cancellations.

Not only are appointment gaps unprofitable and inefficient for healthcare service providers, but they also often represent a significant disservice to other healthcare service consumers, i.e., potential patients, that are often frustrated by the unavailability of appointments with specific healthcare service providers and/or the long waiting periods for an appointment.

In some cases, healthcare service providers try to backfill cancelled appointments, or appointments that have otherwise become available, by scrambling to offer the cancelled appointment time to other patients with later appointments. However, current methods for rescheduling and back-filling cancelled appointments are typically extremely inefficient and involve significant employee time. In addition, current methods for rescheduling and back-filling cancelled appointments are typically done in a hap-hazard manner that rarely is fair and/or even represents any systematic effort to offer the open appointment to the healthcare service consumers who have waited the longest, or have the greatest need. In addition, current methods for rescheduling and back-filling cancelled appointments are typically made by calling a potential fill-in healthcare service consumer and, if the potential fill-in healthcare service consumer does not answer the phone immediately, another potential fill-in healthcare service consumer is called without any follow-up or response time being provided to the first potential fill-in healthcare service consumer.

As a result of the situation described above, current methods for rescheduling and back-filling cancelled appointments are inefficient, arguably unfair, and rarely result in the open appointment actually being filed. In addition, even when the appointment is successfully back-filled, the time and energy involved in rescheduling a replacement healthcare service consumer typically outweighs the gains associated with filling the appointment gap.

SUMMARY

In accordance with one embodiment, a system and method for providing real time appointment rescheduling includes a process for providing real time appointment rescheduling whereby access to one or more computing system implemented appointment scheduling systems is provided. In one embodiment, process for providing real time appointment rescheduling provides a virtual open appointment wait list to be associated with one or more appointment slots in the one or more computing system implemented appointment scheduling systems. In one embodiment, one or more healthcare service consumers request to be placed on the virtual open appointment wait list and provide process for providing real time appointment rescheduling with patient virtual open appointment wait list data including, but not limited to one or more of the following: the healthcare service consumer's name and/or other identification; contact information for the healthcare service consumer including, in one embodiment, mobile device contact information; the name and/or identification for healthcare service provider, or providers, the healthcare service consumer desires to see; the type of appointment desired; and/or a time frame for the desired appointment. In one embodiment, the process for providing real time appointment rescheduling then generates and attaches provider virtual open appointment wait list data to the patient virtual open appointment wait list data. In one embodiment the provider virtual open appointment wait list data includes, but not limited to, one or more of the following: an assigned virtual open appointment wait list data identification code indicating the position on the virtual open appointment wait list assigned to the healthcare service consumer; approximate appointment length associated with the type of appointment indicated in the patient virtual open appointment wait list data; and data indicating any currently assigned appointment for the healthcare service consumer. In one embodiment, the patient and provider virtual open appointment wait list data is stored. In one embodiment, when an appointment becomes available, the patient and provider virtual open appointment wait list data is searched to find a first healthcare service consumer that is next on the virtual open appointment wait list and whose patient and provider virtual open appointment wait list data is consistent with the newly available appointment. In one embodiment, the first healthcare service consumer is contacted in accordance with the patient virtual open appointment wait list data and the first healthcare service consumer is given a designated period of time to respond, i.e., accept or decline the newly available appointment. In one embodiment, after the designated period of time has passed with no response from the first healthcare service consumer, the patient and provider virtual open appointment wait list data is searched again to find a second healthcare service consumer that is next, after the first healthcare service consumer, on the virtual open appointment wait list and whose patient and provider virtual open appointment wait list data is consistent with the newly available appointment. In one embodiment, the second healthcare service consumer is contacted in accordance with the patient virtual open appointment wait list data and the second healthcare service consumer is given a designated period of time to accept or decline the newly available appointment. In one embodiment, this process is repeated automatically until the newly available appointment is accepted by one of the healthcare service consumers on the virtual open appointment wait list. In one embodiment, if the newly available appointment is not accepted by one of the healthcare service consumers on the virtual open appointment wait list during a first pass through the healthcare service consumers on the virtual open appointment wait list, process for providing real time appointment rescheduling begins again with the first healthcare service consumer that did not actively decline the newly available appointment and the process is repeated in a loop fashion automatically until the newly available appointment is accepted by one of the healthcare service consumers on the virtual open appointment wait list.

In one embodiment, the process for providing real time appointment rescheduling is a stand alone system implemented on, or accessed through, a computing system. In one embodiment, the process for providing real time appointment rescheduling is part of, accessible by, or otherwise associated with, a computing system implemented data management system. In one embodiment, the process for providing real time appointment rescheduling is part of, accessible by, or otherwise associated with, a computing system implemented healthcare management system.

In one embodiment, the process for providing real time appointment rescheduling is provided access to one or more computing system implemented appointment scheduling systems that are independent of the process for providing real time appointment rescheduling and/or a computing system implemented data management system implementing, or otherwise associated with, the process for providing real time appointment rescheduling.

In one embodiment, the process for providing real time appointment rescheduling is provided access to one or more computing system implemented appointment scheduling systems that are provided by, implemented by, or otherwise associated with, the process for providing real time appointment rescheduling and/or a computing system implemented data management system implementing, or otherwise associated with, process for providing real time appointment rescheduling.

In one embodiment, the process for providing real time appointment rescheduling is provided access to one or more computing system implemented appointment scheduling systems via a website. In one embodiment, the process for providing real time appointment rescheduling is provided access to one or more computing system implemented appointment scheduling systems by linking to, and/or accessing, one or more databases, and/or computing systems, and/or websites associated with one or more healthcare service providers, and/or one or more healthcare insurance plan administrators. In one embodiment, the process for providing real time appointment rescheduling is provided access to one or more computing system implemented appointment scheduling systems by providing process for providing real time appointment rescheduling, and/or a computing system implemented data management system associated with the process for providing real time appointment rescheduling access to a computing system, and/or a server system, under the control of one or more healthcare service providers. In one embodiment, the process for providing real time appointment rescheduling is provided access to one or more computing system implemented appointment scheduling systems using a computer program product as defined herein. In one embodiment, the process for providing real time appointment rescheduling is provided access to one or more computing system implemented appointment scheduling systems through a network of computing systems and/or server systems that is comprised of multiple different computing systems, wireless devices, cellular telephones, digital telephones, two-way pagers, personal digital assistants, server computers, or any desired combination of these devices, that are interconnected using a network. In one embodiment, the process for providing real time appointment rescheduling is provided access to one or more computing system implemented appointment scheduling systems through e-mail and/ or through text messaging. In one embodiment, the process for providing real time appointment rescheduling is provided access to one or more computing system implemented appointment scheduling systems using screen scraping, or a similar technology, as known in the art at the time of filing, and/or as developed after the time of filing. In one embodiment, the process for providing real time appointment rescheduling is provided access to one or more computing system implemented appointment scheduling systems using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, the process for providing real time appointment rescheduling provides a virtual open appointment wait list to be associated with one or more appointments in the one or more computing system implemented appointment scheduling systems. In one embodiment, each appointment slot is provided its own virtual open appointment wait list capability with eligibility criteria specific to the given appointment slot based on, but not limited to, any one or more of the following: the length of the appointment; the type of services associated with the appointment; the location of the appointment; the healthcare service provider scheduled for the appointment; or any other eligibility criteria specific to the given appointment slot desired.

In one embodiment, one or more healthcare service consumers request to be placed on the virtual open appointment wait list, in one embodiment, after they have already been assigned an appointment that is currently available. For instance, in one embodiment, after a given healthcare service consumer is scheduled for an appointment in two weeks, the given healthcare service consumer is provided the opportunity to be placed on the virtual open appointment wait list for a potentially sooner appointment that may, or may not, become available. In one embodiment, the given healthcare service provider requests to be placed on the virtual open appointment wait list by indicating verbally their desire to the healthcare service provider, or the healthcare service provider's employees. In one embodiment, the given healthcare service provider requests to be placed on the virtual open appointment wait list by indicating their desire to the healthcare service provider, or the healthcare service provider's employees, via e-mail or through a website. In one embodiment, the given healthcare service provider requests to be placed on the virtual open appointment wait list by indicating their desire to the healthcare service provider, or the healthcare service provider's employees, using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, a given healthcare service consumer requesting to be placed on the virtual open appointment wait list provides process for providing real time appointment rescheduling with patient virtual open appointment wait list data. In one embodiment, the patient virtual open appointment wait list data includes, but not limited to, one or more of the following: the healthcare service consumer's name and/or other identification; contact information for the healthcare service consumer including, in one embodiment, mobile device contact information, such as a cell phone or pager number; the name and/or identification for healthcare service provider, or providers, desired to be seen; the type of appointment desired; and/or a time frame for the desired appointment.

In one embodiment, all, or part of, the patient virtual open appointment wait list data associated with a given healthcare service consumer is obtained from the healthcare service consumer directly. In one embodiment, all, or part of, the patient virtual open appointment wait list data associated with a given healthcare service consumer is obtained from a mobile computing device associated with the healthcare service consumer. In one embodiment, all, or part of, the patient virtual open appointment wait list data associated with a given healthcare service consumer is obtained from a computing system implemented data management system associated with the healthcare service consumer and/or the healthcare service provider. In one embodiment, all, or part of, the patient virtual open appointment wait list data associated with a given healthcare service consumer is obtained from a computing system implemented healthcare management system associated with the healthcare service consumer and/or the healthcare service provider.

In one embodiment, the process for providing real time appointment rescheduling then attaches provider virtual open appointment wait list data to the patient virtual open appointment wait list data such as, but not limited to, one or more of the following: an assigned virtual open appointment wait list data identification code indicating the position on the virtual open appointment wait list assigned to the healthcare service consumer; approximate appointment length associated with the type of appointment indicated in the patient virtual open appointment wait list data; and data indicating the currently assigned appointment for the healthcare service consumer.

In one embodiment, all, or part of, the provider virtual open appointment wait list data is entered by the healthcare service provider and/or an employee of the healthcare service provider directly. In one embodiment, all, or part of, the provider virtual open appointment wait list data is obtained from a computing system associated with the healthcare service provider. In one embodiment, all, or part of, the provider virtual open appointment wait list data is obtained from a computing system implemented data management system associated with the healthcare service provider. In one embodiment, all, or part of, the provider virtual open appointment wait list data is obtained from a computing system implemented healthcare management system associated with the healthcare service provider.

In one embodiment, once the patient and provider virtual open appointment wait list data is obtained, the data is stored, in whole, or in part, in a memory system, such as one or more databases, or in a cache memory, or in any main memory or mass memory, associated with a computing system. In one embodiment, the data, in whole, or in part, is stored in any computing system and/or server system, or other device, in another location, or on/in a computer readable medium, and/or any other computer program product, as defined herein. In one embodiment, the data, in whole, or in part, is stored on a webpage, in a web-based system or on a public network such as the Internet.

In one embodiment, when an appointment becomes available, the patient and provider virtual open appointment wait list data is searched to find a first healthcare service consumer that is next on the virtual open appointment wait list, and whose patient and provider virtual open appointment wait list data is consistent with the newly available appointment.

For instance, in one embodiment, the patient and provider virtual open appointment wait list data is searched to find a first healthcare service consumer having an assigned virtual open appointment wait list data identification code indicating he or she is in the first, or next, position on the virtual open appointment wait list. In this way potential healthcare service consumers can be offered the newly available appointment in an order reflective of the time they have waited for an appointment, i.e., on a first come, first served, basis.

In one embodiment, the patient and provider virtual open appointment wait list data is searched to find a first healthcare service consumer on the virtual open appointment wait list that has indicated a desire to see the specific healthcare service provider associated with the newly available appointment. In this way a healthcare service consumer is provided the opportunity to accept only appointments that become available with a specific healthcare service provider.

In one embodiment, the patient and provider virtual open appointment wait list data is searched to find a first healthcare service consumer on the virtual open appointment wait list desiring an appointment having an approximate appointment length associated with the newly available appointment. In this way healthcare service consumers are only offered the newly available appointments that meet their time needs. For instance, healthcare service consumers requiring a 60 minute appointment are not offered 30 minute appointment slots.

In one embodiment, the patient and provider virtual open appointment wait list data is searched to find a first healthcare service consumer on the virtual open appointment wait list desiring an appointment in a time frame consistent with the newly available appointment. In this instance, the healthcare service consumer is not offered a newly available appointment that they cannot make, such as an appointment that becomes available when they are out-of-town, or must work.

In one embodiment, the patient and provider virtual open appointment wait list data is searched to find a first healthcare service consumer on the virtual open appointment wait list desiring a type of appointment consistent with the newly available appointment. In this case, the healthcare service consumer is offered newly available appointments that meet their needs. For instance, a given healthcare service provider may only perform annual physicals on Tuesdays. In this case, a healthcare service consumer needing a physical will only be offered newly available appointments on Tuesdays.

In one embodiment, one or more of the healthcare service consumers on the virtual open appointment wait list have mobile computing systems, such as a cellular phone, that include global positioning satellite capability, or a similar positioning capability. In these instances, and particularly when an appointment becomes available on very short notice, the healthcare service consumers closet to the healthcare service provider's office when the appointment becomes available are offered newly available appointments first.

In one embodiment, the first healthcare service consumer that is next on the virtual open appointment wait list, and whose patient and provider virtual open appointment wait list data is consistent with the newly available appointment, is contacted in accordance with the patient virtual open appointment wait list data. In one embodiment, the first healthcare service consumer is contacted via a mobile computing system such as, but not limited to: a cellular phone; a pager; a text messaging device; a PDA; a car phone; etc. In one embodiment, the first healthcare service consumer is contacted via any computing system. In one embodiment, the first healthcare service consumer is contacted via traditional telephone service. In one embodiment, the first healthcare service consumer is contacted via postal service. In one embodiment, the first healthcare service consumer is contacted via a website. In one embodiment, the first healthcare service consumer is contacted by linking to, and/or accessing, one or more databases, and/or computing systems, and/or websites associated with one or more healthcare service providers, and/or one or more healthcare insurance plan administrators. In one embodiment, the first healthcare service consumer is contacted via a computer program product as defined herein. In one embodiment, the first healthcare service consumer is contacted through a network of computing systems and/or server systems that is comprised of multiple different computers, wireless devices, cellular telephones, digital telephones, two-way pagers, personal digital assistants, server computers, or any desired combination of these devices, that are interconnected using a network. In one embodiment, the first healthcare service consumer is contacted e-mail and/or through text messaging. In one embodiment, the first healthcare service consumer is contacted using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, when the first healthcare service consumer is contacted, the first healthcare service consumer is given a designated period of time to respond and accept, or decline, the newly available appointment. In one embodiment, the designated period of time is determined based how much time is available between when the first healthcare service consumer is contacted and newly available appointment time. For instance, in the case of a same day newly available appointment time, the designated period of time to respond and accept may be a matter of minutes or hours. On the other hand, in the case of a newly available appointment time weeks in the future, the designated period of time to respond and accept or decline may be a matter of days.

In one embodiment, if the first healthcare service consumer responds within the designated period of time to respond and accept, the first healthcare service consumer is given the newly available appointment. In one embodiment, if the first healthcare service consumer had a previously scheduled appointment, then, when the first healthcare service consumer is given the newly available appointment, the previously scheduled appointment becomes a newly available appointment, and the process for providing real time appointment rescheduling repeats itself for this newly available appointment.

On the other hand, in one embodiment, if the first healthcare service consumer declines the newly available appointment and/or fails to respond within the designated period of time to respond and accept, after the designated period of time has passed, the patient and provider virtual open appointment wait list data is searched again to find a second healthcare service consumer that is next, after the first healthcare service consumer, on the virtual open appointment wait list, and whose patient and provider virtual open appointment wait list data is consistent with the newly available appointment. In one embodiment, the second healthcare service consumer is contacted in accordance with the patient virtual open appointment wait list data and the second healthcare service consumer is given a designated period of time to respond and accept or decline the newly available appointment. In one embodiment, this process is repeated automatically until the newly available appointment is accepted by one of the healthcare service consumers on the virtual open appointment wait list.

In one embodiment, if the newly available appointment is not accepted by any of the healthcare service consumers on the virtual open appointment wait list during a first pass through the healthcare service consumers on the virtual open appointment wait list, process for providing real time appointment rescheduling begins again with the first healthcare service consumer that did not actively decline the newly available appointment and the process is repeated in a loop fashion automatically until the newly available appointment is accepted by one of the healthcare service consumers on the virtual open appointment wait list.

Using the process for providing real time appointment rescheduling, as disclosed herein, healthcare service providers can backfill cancelled appointments, or appointments that have otherwise become available, in a systematic and automatic manner without using significant employee time and energy. Consequently, using the process for providing real time appointment rescheduling, as disclosed herein, healthcare service providers can backfill cancelled appointments, or appointments that have otherwise become available, in fair efficient manner that benefits both healthcare service providers and their healthcare service consumers.

Figure 1:
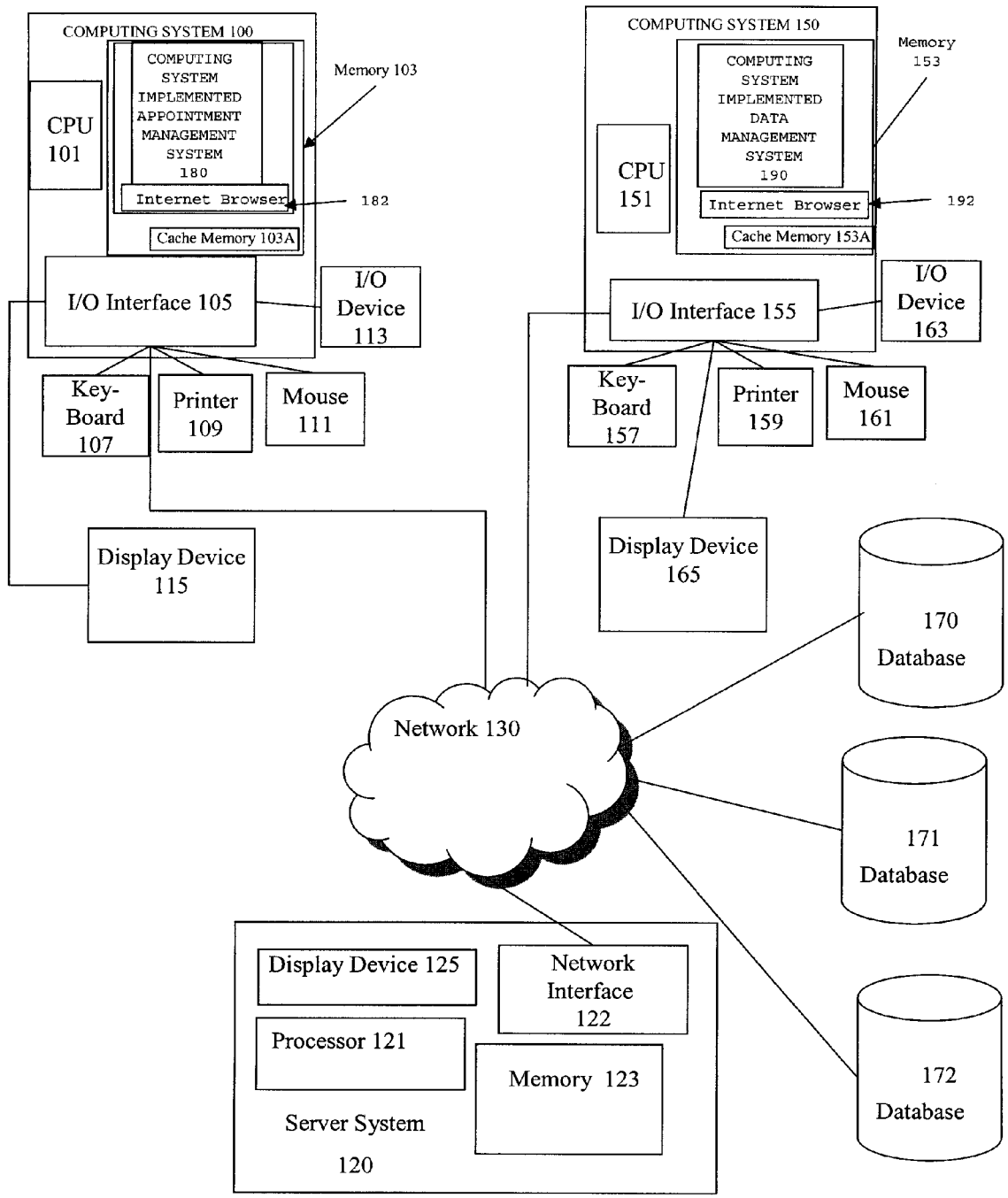
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

In accordance with one embodiment, a system and method for providing real time appointment rescheduling includes a process for providing real time appointment rescheduling whereby access to one or more computing system implemented appointment scheduling systems is provided. In one embodiment, process for providing real time appointment rescheduling provides a virtual open appointment wait list to be associated with one or more appointment slots in the one or more computing system implemented appointment scheduling systems. In one embodiment, one or more healthcare service consumers request to be placed on the virtual open appointment wait list and provide process for providing real time appointment rescheduling with patient virtual open appointment wait list data including, but not limited to one or more of the following: the healthcare service consumer's name and/or other identification; contact information for the healthcare service consumer including, in one embodiment, mobile device contact information; the name and/or identification for healthcare service provider, or providers, the healthcare service consumer desires to see; the type of appointment desired; and/or a time frame for the desired appointment. In one embodiment, the process for providing real time appointment rescheduling then generates and attaches provider virtual open appointment wait list data to the patient virtual open appointment wait list data. In one embodiment the provider virtual open appointment wait list data includes, but not limited to, one or more of the following: an assigned virtual open appointment wait list data identification code indicating the position on the virtual open appointment wait list assigned to the healthcare service consumer; approximate appointment length associated with the type of appointment indicated in the patient virtual open appointment wait list data; and data indicating any currently assigned appointment for the healthcare service consumer. In one embodiment, the patient and provider virtual open appointment wait list data is stored. In one embodiment, when an appointment becomes available, the patient and provider virtual open appointment wait list data is searched to find a first healthcare service consumer that is next on the virtual open appointment wait list and whose patient and provider virtual open appointment wait list data is consistent with the newly available appointment. In one embodiment, the first healthcare service consumer is contacted in accordance with the patient virtual open appointment wait list data and the first healthcare service consumer is given a designated period of time to respond, i.e., accept or decline the newly available appointment. In one embodiment, after the designated period of time has passed with no response from the first healthcare service consumer, the patient and provider virtual open appointment wait list data is searched again to find a second healthcare service consumer that is next, after the first healthcare service consumer, on the virtual open appointment wait list and whose patient and provider virtual open appointment wait list data is consistent with the newly available appointment. In one embodiment, the second healthcare service consumer is contacted in accordance with the patient virtual open appointment wait list data and the second healthcare service consumer is given a designated period of time to accept or decline the newly available appointment. In one embodiment, this process is repeated automatically until the newly available appointment is accepted by one of the healthcare service consumers on the virtual open appointment wait list. In one embodiment, if the newly available appointment is not accepted by one of the healthcare service consumers on the virtual open appointment wait list during a first pass through the healthcare service consumers on the virtual open appointment wait list, process for providing real time appointment rescheduling begins again with the first healthcare service consumer that did not actively decline the newly available appointment and the process is repeated in a loop fashion automatically until the newly available appointment is accepted by one of the healthcare service consumers on the virtual open appointment wait list.

Hardware System Architecture

FIG. 1 is a block diagram of an exemplary hardware architecture for implementing one embodiment of a system and method for providing real time appointment rescheduling, such as exemplary process 200 (FIG. 2) discussed herein, that, returning to FIG. 1, includes: a computing system 100, e.g., a first computing system; a computing system 150, e.g., a second computing system; a server system 120; and exemplary databases 170, 171, and/or 172, all operatively coupled by a network 130.

As seen in FIG. 1, computing system 100 typically includes a central processing unit (CPU) 101, an input/output (I/O) interface 105, and a memory system 103, including cache memory 103A. In one embodiment, memory system 103 includes all, or part, of a computing system implemented appointment management system 180, such as any computing system implemented appointment management system discussed herein, and/or known in the art at the time of filing, and/or as developed thereafter. In one embodiment, computing system implemented appointment management system 180 is stored, in whole, or in part, in memory system 103, and is used by, or includes, or is accessed by, one or more healthcare providers and/or healthcare service consumers, and/or a process for providing real time appointment rescheduling.

Returning to FIG. 1, computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, computing system 100, whether available or known at the time of filing or as later developed. In one embodiment, a process for providing real time appointment rescheduling and/or a computing system implemented appointment management system are entered, in whole, or in part, into computing system 100 via I/O device 113, such as from a CD, DVD, floppy disk, portable hard drive, memory stick, download site, or other medium and/or computer program product as defined herein.

In one embodiment, computing system 100 also includes an Internet browser capability 182 that, in one embodiment, includes a search engine (not shown) and is stored, in whole, or in part in memory 103.

In one embodiment, computing system 100 is used by, or includes, or is accessed by, one or more healthcare service providers and memory system 103 includes all, or part, of provider virtual open appointment wait list data and/or patient virtual open appointment wait list data associated with one or more healthcare service consumers and/or a data representing a virtual open appointment wait list. In one embodiment, computing system 100 is a computing system accessible by one or more healthcare service consumers for making healthcare service appointments. In one embodiment, computing system 100 is a computing system accessible by a process for providing real time appointment rescheduling. In one embodiment, computing system 100 is used, and/or accessible, by another computing system, such as computing system 150 (discussed below).

Computing system 100 can be any computing system as defined herein and/or as known in the art at the time of filing and/or as developed thereafter, that includes components that can execute all, or part, of a process for providing real time appointment rescheduling, and/or a computing system implemented appointment management system, in accordance with at least one of the embodiments as described herein.

Similarly, computing system 150 typically includes a CPU 151, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, whether available or known at the time of filing or as later developed.

In one embodiment, computing system 150 also includes an Internet browser capability 192 that, in one embodiment, includes a search engine (not shown) and is stored, in whole, or in part in memory 153.

In one embodiment, memory system 153 includes all, or part, of a computing system implemented data management system 190, such as any computing system implemented data management system defined herein, known in the art at the time of filing, and/or as developed thereafter. In one embodiment, computing system implemented data management system 190 is a computing system implemented healthcare management system. In one embodiment, computing system implemented data management system 190 is stored, in whole, or in part, in memory system 153, and is used by, or includes, or is accessed by, a process for providing real time appointment rescheduling.

In one embodiment, computing system 150 is a mobile computing system such as, but not limited to, a mobile phone, a mobile pager, a text messaging device, or a PDA.

In one embodiment, computing system 150 is used by, or is accessed by, one or more healthcare service consumers and memory system 153 includes all, or part, of data representing patient virtual open appointment wait list data and/or provider virtual open appointment wait list data and/or virtual open appointment wait list data. In one embodiment, computing system 150 is a computing system accessible by one or more healthcare service providers. In one embodiment, computing system 150 is a computing system accessible by a process for providing real time appointment rescheduling. In one embodiment, computing system 150 is used, and/or accessible, by another computing system, such as computing system 100.

Computing system 150 can be any computing system as defined herein and/or as known in the art at the time of filing and/or as developed thereafter, that includes components that can execute all, or part, of a process for providing real time appointment rescheduling, and/or a computing system implemented data management system, in accordance with at least one of the embodiments as described herein.

As discussed in more detail below, in one embodiment, all, or part, of a process for providing real time appointment rescheduling, and/or a computing system implemented data management system, and/or a computing system implemented appointment management system, and/or data representing a virtual open appointment wait list, and/or patient virtual open appointment wait list data and/or provider virtual open appointment wait list data can be loaded, in whole, or in part, into computing system 150 from computing system 100 for storage in memory system 153 and/or cache memory 153A.

Also shown in FIG. 1 are databases 170, 171, and/or 172. In one embodiment, one or more of databases 170, 171, and/or 172 is a data storage device, a designated server system or computing system, or a designated portion of one or more server systems or computing systems, such as computing systems 100, 150 and server system 120, or a distributed database, or an external and/or portable hard drive. In one embodiment, one or more of databases 170, 171, and/or 172 is a dedicated mass storage device implemented in software, hardware, or a combination of hardware and software. In one embodiment, one or more of databases 170, 171, and/or 172 include a web-based function. As discussed in more detail below, in one embodiment, one or more of databases 170, 171, and/or 172 is under the control of includes, or is accessed by, one or more healthcare service providers and/or healthcare service consumers and one or more of databases 170, 171, and/or 172 includes all, or part, of a process for providing real time appointment rescheduling, and/or a computing system implemented data management system, and/or a computing system implemented appointment management system, and/or data representing a virtual open appointment wait list, and/or patient virtual open appointment wait list data and/or provider virtual open appointment wait list data.

In one embodiment, one or more of databases 170, 171, and/or 172 is used, and/or accessible, by a computing system, such as computing systems 100 and/or 150, and/or a server system, such as sever system 120 (discussed below). In one embodiment, one or more of databases 170, 171, and/or 172 is used, controlled, and/or accessible by, a provider of and/or a computing system implemented data management system.

In one embodiment, computing systems 100 and 150, and databases 170, 171, and/or 172, are coupled to a server system 120 through network 130. In one embodiment, server system 120 includes a server system display device 125, a server system processor 121, a server system memory 123, and a server system network interface 122.

In one embodiment, server system 120 is used in a station-to-station arrangement, such as a peer-to-peer, or hybrid peer-to peer, arrangement, as an indexing and/or central server used to connect a first computing system, such as computing system 100, and a second computing system, such as computing system 150.

In one embodiment, all, or part, of a process for providing real time appointment rescheduling, and/or a computing system implemented data management system, and/or a computing system implemented appointment management system, and/or data representing a virtual open appointment wait list, and/or patient virtual open appointment wait list data and/or provider virtual open appointment wait list data is stored in server system 120, and is used by, or is accessed by, a process for providing real time appointment rescheduling. In one embodiment, server system 120 is accessible by one or more healthcare service providers, and/or one or more healthcare service consumers, and/or a provider of and/or a computing system implemented data management system. In one embodiment, server system 120 is used, and/or accessible, by a computing system, such as computing systems 100 and/or 150, and/or one or more databases, such as databases 170, 171, and/or 172.

Network 130 can be any network or network system as defined herein, and/or known in the art at the time of filing, and/or as developed after the time of filing, capable of allowing communication between two or more computing systems, server systems, and/or databases.

Those of skill in the art will readily recognize that the components shown in FIG. 1, such as computing systems 100 and 150, databases 170, 171, and/or 172, server system 120, and their respective components, are shown for illustrative purposes only and that architectures with more or fewer components can implement, and benefit from, the invention. Moreover, one or more components of computing system 100, computing system 150, databases 170, 171, and/or 172, and server system 120 may be located remotely from their respective system and accessed via network 130. In addition, the particular type of, and configuration of, computing systems 100 and 150, databases 170, 171, and/or 172, and server system 120 are not relevant.

As discussed in more detail below, in one embodiment, all, or part, of a process for providing real time appointment rescheduling, and/or a computing system implemented data management system, and/or a computing system implemented appointment management system, and/or data representing a virtual open appointment wait list, and/or patient virtual open appointment wait list data and/or provider virtual open appointment wait list data, is stored in memory system 103 and/or cache memory 103A, of computing system 100, and/or memory system 153 and/or cache memory 153A of computing system 150, and/or in server memory system 123 of server system 120, and/or in databases 170, 171, and/or 172, and executed on computing system 100 and/or computing system 150. As used herein, a memory refers to a volatile memory, a non-volatile memory, or any combination of the two.

Although a process for providing real time appointment rescheduling, and/or a computing system implemented data management system, and/or a computing system implemented appointment management system, are sometimes referred to herein, alternatively, as a process, an application, a module, a program, a component of a software system, a component of a software package, a component of a parent system, a plug-in, or a feature of a parent system, this terminology is illustrative only. In some embodiments, a process for providing real time appointment rescheduling, and/or a computing system implemented data management system, and/or a computing system implemented appointment management system are capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPUs 101 and 151, or server system processor 121. In one embodiment, execution of a process by CPU 101, CPU 151, or server system processor 121, results in the operations of an agent computer process (not shown) and/or a rule computer process (not shown).

In one embodiment, all, or part, of a process for providing real time appointment rescheduling, and/or a computing system implemented data management system, and/or a computing system implemented appointment management system, and/or data representing a virtual open appointment wait list, and/or patient virtual open appointment wait list data and/or provider virtual open appointment wait list data, are computer applications or processes and/or data implemented and/or run and/or stored, in full, or in part, in, or on, and/or through, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable data representing computer readable code, whether available or known at the time of filing or as later developed. This medium may belong to a computing system, such as computing systems 100 and 150 of FIG. 1, described above. However, in some embodiments, the medium also may be removable and/or remote from the computing system.

Process

Herein, the terms "healthcare service consumer", "healthcare services consumer", "healthcare consumer" "service consumer" and "patient" and/or "consumer", are used to denote any person, party, or parties, who receive healthcare services from a healthcare services provider, and/or an authorized agent of any person, party, or parties, who receive healthcare services from a healthcare services provider.

Herein, the term "healthcare service provider" and/or "healthcare provider" denotes any individual person, persons, agencies, institutions, organizations, businesses, and/or other entities that provide medical treatment, medications, therapy, advice, and/or equipment. For example, herein, the term "healthcare service provider" includes, but is not limited to: doctors; nurses; technicians; therapists; pharmacists; laboratories; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the terms "healthcare" and/or "healthcare service" denote any general and/or specialized treatment, assessment, maintenance, therapy, medication, and/or advice relating to all, or any portion of, a healthcare service consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; lab work, recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare service consumer's state of health.

Herein, the terms "healthcare insurance plan", "healthcare benefit plan", and "health insurance program" are used interchangeably to denote any policy, program, means and/or mechanism whereby a healthcare service consumer is provided healthcare benefits and/or healthcare services and/or entitlements to any from of healthcare.

Herein, the terms "healthcare insurance provider", "healthcare insurance service provider", "health insurance plan provider" and "health services insurance provider" are used interchangeably to denote any individual person, persons, agencies, institutions, organizations, businesses, and/or other entities that provide one or more healthcare insurance plans.

Herein, the terms "healthcare insurance plan administrator", "healthcare insurance service plan administrator", "health insurance plan administrator" and "health services insurance plan administrator" are used interchangeably to denote any individual person, persons, agencies, institutions, organizations, businesses, and/or other entities that administer and/or regulate and/or monitor one or more healthcare insurance plans.

As used herein, the term "computing system", denotes, but is not limited to: a portable computer; a workstation; a two-way pager; a cellular telephone; a smart phone; a digital wireless telephone; a Personal Digital Assistant (PDA); a media player, i.e., an MP3 player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "computing system implemented data management system" includes, but is not limited to: computing system implemented appointment management systems, packages, programs, modules, or applications; computing system implemented personal and small business healthcare management systems, packages, programs, modules, or applications; computing system implemented personal and small business financial management systems, packages, programs, modules, or applications; computing system implemented business systems, packages, programs, modules, or applications; computing system implemented healthcare provider office management systems, packages, programs, modules, or applications; computing system implemented payroll management systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented accounting and/or invoicing systems, packages, programs, modules, or applications; computing system implemented business and/or point of sale systems, packages, programs, modules, or applications; and various other electronic data driven data management systems, packages, programs, modules, or applications, whether known at the time of filing or as developed later.

As used herein, the term "network" is used to denote any network or network system such as, but not limited to, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, whether available or known at the time of filing or as later developed.

As used herein, the term "database" is used to define any data storage mechanism known at the time of filing or as developed thereafter, such as, but not limited to: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based function. Herein, the term "database" can refer to data storage means that is part of, or under the control of, any computing system, as defined herein, and/or known at the time of filing, and/or as developed thereafter.

In accordance with one embodiment, a system and method for providing real time appointment rescheduling includes a process for providing real time appointment rescheduling whereby access to one or more computing system implemented appointment scheduling systems is provided. In one embodiment, process for providing real time appointment rescheduling provides a virtual open appointment wait list to be associated with one or more appointment slots in the one or more computing system implemented appointment scheduling systems. In one embodiment, one or more healthcare service consumers request to be placed on the virtual open appointment wait list and provide process for providing real time appointment rescheduling with patient virtual open appointment wait list data including, but not limited to one or more of the following: the healthcare service consumer's name and/or other identification; contact information for the healthcare service consumer including, in one embodiment, mobile device contact information; the name and/or identification for healthcare service provider, or providers, the healthcare service consumer desires to see; the type of appointment desired; and/or a time frame for the desired appointment. In one embodiment, the process for providing real time appointment rescheduling then generates and attaches provider virtual open appointment wait list data to the patient virtual open appointment wait list data. In one embodiment the provider virtual open appointment wait list data includes, but not limited to, one or more of the following: an assigned virtual open appointment wait list data identification code indicating the position on the virtual open appointment wait list assigned to the healthcare service consumer; approximate appointment length associated with the type of appointment indicated in the patient virtual open appointment wait list data; and data indicating any currently assigned appointment for the healthcare service consumer. In one embodiment, the patient and provider virtual open appointment wait list data is stored. In one embodiment, when an appointment becomes available, the patient and provider virtual open appointment wait list data is searched to find a first healthcare service consumer that is next on the virtual open appointment wait list and whose patient and provider virtual open appointment wait list data is consistent with the newly available appointment. In one embodiment, the first healthcare service consumer is contacted in accordance with the patient virtual open appointment wait list data and the first healthcare service consumer is given a designated period of time to respond, i.e., accept or decline the newly available appointment. In one embodiment, after the designated period of time has passed with no response from the first healthcare service consumer, the patient and provider virtual open appointment wait list data is searched again to find a second healthcare service consumer that is next, after the first healthcare service consumer, on the virtual open appointment wait list and whose patient and provider virtual open appointment wait list data is consistent with the newly available appointment. In one embodiment, the second healthcare service consumer is contacted in accordance with the patient virtual open appointment wait list data and the second healthcare service consumer is given a designated period of time to accept or decline the newly available appointment. In one embodiment, this process is repeated automatically until the newly available appointment is accepted by one of the healthcare service consumers on the virtual open appointment wait list. In one embodiment, if the newly available appointment is not accepted by one of the healthcare service consumers on the virtual open appointment wait list during a first pass through the healthcare service consumers on the virtual open appointment wait list, process for providing real time appointment rescheduling begins again with the first healthcare service consumer that did not actively decline the newly available appointment and the process is repeated in a loop fashion automatically until the newly available appointment is accepted by one of the healthcare service consumers on the virtual open appointment wait list.

Figure 2:
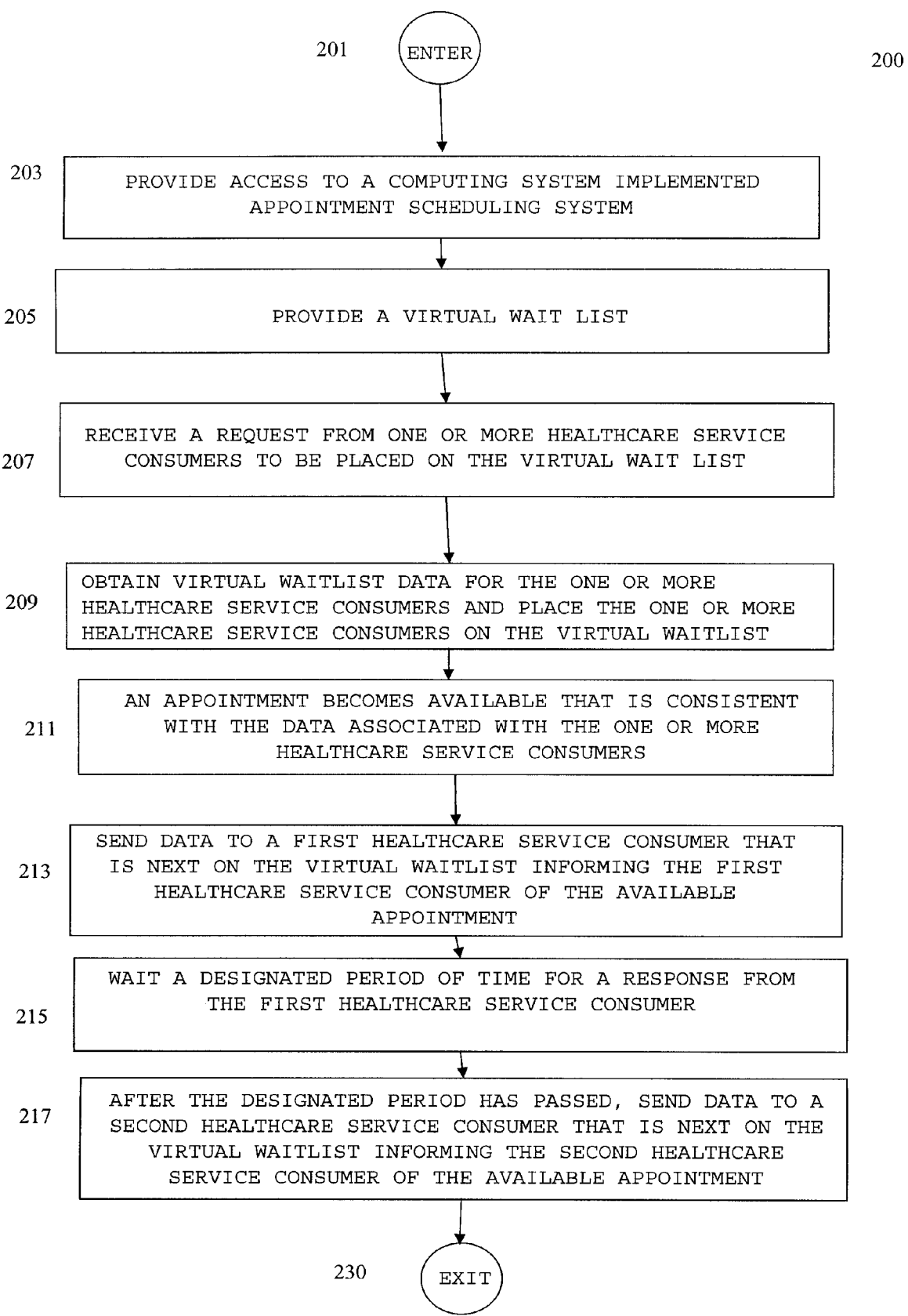
FIG. 2 is a flow chart depicting a process for providing real time appointment rescheduling in accordance with one embodiment.

FIG. 2 a flow chart depicting a process for providing real time appointment rescheduling 200 in accordance with one embodiment. Process for providing real time appointment rescheduling 200 begins at ENTER OPERATION 201 of FIG. 2 and process flow proceeds to PROVIDE ACCESS TO A COMPUTING SYSTEM IMPLEMENTED APPOINTMENT SCHEDULING SYSTEM OPERATION 203.

In one embodiment, at PROVIDE ACCESS TO A COMPUTING SYSTEM IMPLEMENTED APPOINTMENT SCHEDULING SYSTEM OPERATION 203 access to one or more computing system implemented appointment scheduling systems is provided to process for providing real-time appointment rescheduling 200.

In one embodiment, process for providing real time appointment rescheduling 200 is a stand alone system implemented on, or accessed through, a computing system, such as computing systems 100 and/150 of FIG. 1 and/or a server system, such as server system 120 of FIG. 1.

Returning to FIG. 2, in one embodiment, process for providing real time appointment rescheduling 200 is part of, accessible by, or otherwise associated with, a computing system implemented data management system, such as computing system implemented data management system 190 of FIG. 1. Returning to FIG. 2, in one embodiment, process for providing real time appointment rescheduling 200 is part of, accessible by, or otherwise associated with, a computing system implemented healthcare management system.

In one embodiment, process for providing real time appointment rescheduling 200 is provided access to one or more computing system implemented appointment scheduling systems, such as computing system implemented appointment scheduling system 180 of FIG. 1, that are independent of process for providing real time appointment rescheduling 200 (FIG. 2) and/or a computing system implemented data management system implementing, or otherwise associated with, process for providing real time appointment rescheduling 200.

In one embodiment, process for providing real time appointment rescheduling 200 is provided access to one or more computing system implemented appointment scheduling systems that are provided by, implemented by, or otherwise associated with, process for providing real time appointment rescheduling 200 and/or a computing system implemented data management system implementing, or otherwise associated with, process for providing real time appointment rescheduling.

In one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems via a one or more websites and/or web-based systems.

In one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems through a parent computing system implemented data management system, such as computing system implemented data management systems 190 of FIG. 1.

Returning to FIG. 2, in one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems by linking to, and/or accessing, one or more databases, such as databases 170, 171 and/or 172 of FIG. 1, and/or computing systems, such as computing system 180 of FIG. 1, and/or websites associated with one or more healthcare service providers, and/or one or more healthcare insurance plan administrators.

Returning to FIG. 2, in one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems via a user interface on a computing system display, such as computing system display device 115 of computing system 100 of FIG. 1, and a user interface device, such as keyboard 107, 157, mouse 111, 161 of FIG. 1 or a touchpad, voice command recognition system, or any other device capable of providing user input to a computing system or for translating user actions into computing system operations, whether available or known at the time of filing or as developed later.

Returning to FIG. 2, in one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems by providing process for providing real time appointment rescheduling 200, and/or a computing system implemented data management system associated with process for providing real time appointment rescheduling 200, access to the data on a database, such as databases 170, 171, and/or 172 of FIG. 1, a computing system, such as computing systems 100 and/or 150 of FIG. 1, and/or a server system, such as server system 120 of FIG. 1, and/or using a computer program product as defined herein.

Returning to FIG. 2, in one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1.

Returning to FIG. 2, in one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems data through e-mail and/or through text messaging.

In one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems data using screen scraping, or a similar technology, as known in the art at the time of filing, and/or as developed after the time of filing.

In one embodiment, at PROVIDE ACCESS TO A COMPUTING SYSTEM IMPLEMENTED APPOINTMENT SCHEDULING SYSTEM OPERATION 203, process for providing real time appointment rescheduling 200 is provided access to one or more computing system implemented appointment scheduling systems using any method, apparatus, process or mechanism for accessing and/or transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

Methods, means, and mechanisms for providing, accessing, entering, transferring, downloading, and/or otherwise obtaining data are well known to those of skill in the art. Consequently a more detailed discussion of the methods, means, and mechanisms for providing, entering, transferring, downloading, and/or otherwise obtaining data are omitted here to avoid detracting from the invention.

In one embodiment, once access to one or more computing system implemented appointment scheduling systems is provided to process for providing real-time appointment rescheduling 200 at PROVIDE ACCESS TO A COMPUTING SYSTEM IMPLEMENTED APPOINTMENT SCHEDULING SYSTEM OPERATION 203, process flow proceeds to PROVIDE A VIRTUAL WAIT LIST OPERATION 205.

In one embodiment, at PROVIDE A VIRTUAL WAIT LIST OPERATION 205 process for providing real time appointment rescheduling 200 provides a virtual open appointment wait list to be associated with one or more appointment slots in the one or more computing system implemented appointment scheduling systems.

In one embodiment, at PROVIDE A VIRTUAL WAIT LIST OPERATION 205 process for providing real time appointment rescheduling 200 generates a general virtual open appointment wait list for any one or more appointment slots in the one or more computing system implemented appointment scheduling systems.

In one embodiment, at PROVIDE A VIRTUAL WAIT LIST OPERATION 205 process for providing real time appointment rescheduling 200 generates a virtual open appointment wait list and electronically associates and/or attaches the virtual open appointment wait list to each of the one or more appointment slots in the one or more computing system implemented appointment scheduling systems.

In one embodiment, at PROVIDE A VIRTUAL WAIT LIST OPERATION 205 each appointment slot in the one or more computing system implemented appointment scheduling systems is provided its own virtual open appointment wait list capability with eligibility criteria specific to the given appointment slot. In one embodiment, the eligibility criteria specific to the given appointment slot is based on, but not limited to, any one or more of the following: the length of the appointment slot in terms of time allotted to the appointment slot; the type of services associated with the appointment slot, such full physical or general service; the office location of the appointment slot; the healthcare service provider scheduled for the appointment and/or any specialists or equipment required for the services associated with the appointment slot; or any other eligibility criteria specific to the given appointment slot desired.

In one embodiment, once process for providing real time appointment rescheduling 200 provides a virtual open appointment wait list to be associated with one or more appointment slots in the one or more computing system implemented appointment scheduling systems at PROVIDE A VIRTUAL WAIT LIST OPERATION 205, process flow proceeds to RECEIVE A REQUEST FROM ONE OR MORE HEALTHCARE SERVICE CONSUMERS TO BE PLACED ON THE VIRTUAL WAIT LIST OPERATION 207.

In one embodiment, at RECEIVE A REQUEST FROM ONE OR MORE HEALTHCARE SERVICE CONSUMERS TO BE PLACED ON THE VIRTUAL WAIT LIST OPERATION 207 one or more healthcare service consumers request to be placed on the given virtual open appointment wait list of PROVIDE A VIRTUAL WAIT LIST OPERATION 205.

In one embodiment, at RECEIVE A REQUEST FROM ONE OR MORE HEALTHCARE SERVICE CONSUMERS TO BE PLACED ON THE VIRTUAL WAIT LIST OPERATION 207 one or more healthcare service consumers request to be placed on a given virtual open appointment wait list of PROVIDE A VIRTUAL WAIT LIST OPERATION 205, in one embodiment, after they have already been assigned an appointment that is currently available. For instance, in one embodiment, after a given healthcare service consumer is scheduled for an appointment in two weeks, the given healthcare service consumer is provided the opportunity to be placed on the virtual open appointment wait list for a potentially sooner appointment that may, or may not, become available.

In one embodiment, at RECEIVE A REQUEST FROM ONE OR MORE HEALTHCARE SERVICE CONSUMERS TO BE PLACED ON THE VIRTUAL WAIT LIST OPERATION 207 one or more healthcare service consumers request to be placed on a given virtual open appointment wait list of PROVIDE A VIRTUAL WAIT LIST OPERATION 205 by verbally, either in-person or by telephone, or by any other audio mechanism, making their request to the healthcare service provider, or the healthcare service provider's employees.

In one embodiment, at RECEIVE A REQUEST FROM ONE OR MORE HEALTHCARE SERVICE CONSUMERS TO BE PLACED ON THE VIRTUAL WAIT LIST OPERATION 207 one or more healthcare service consumers request to be placed on a given virtual open appointment wait list of PROVIDE A VIRTUAL WAIT LIST OPERATION 205 by via e-mail, text messaging, or through a website.

In one embodiment, at RECEIVE A REQUEST FROM ONE OR MORE HEALTHCARE SERVICE CONSUMERS TO BE PLACED ON THE VIRTUAL WAIT LIST OPERATION 207 one or more healthcare service consumers request to be placed on a given virtual open appointment wait list of PROVIDE A VIRTUAL WAIT LIST OPERATION using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, once one or more healthcare service consumers request to be placed on the virtual open appointment wait list of PROVIDE A VIRTUAL WAIT LIST OPERATION 205 at RECEIVE A REQUEST FROM ONE OR MORE HEALTHCARE SERVICE CONSUMERS TO BE PLACED ON THE VIRTUAL WAIT LIST OPERATION 207, process flow proceeds to OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 virtual waitlist data required to place a healthcare service provider on the virtual open appointment wait list is provided to process for providing real time appointment rescheduling 200.

In one embodiment, at OBTAIN VIRTUAL WAITLIST DATA FOR THE ONE OR MORE HEALTHCARE SER- VICE CONSUMERS AND PLACE THE ONE OR MORE HEALTHCARE SERVICE CONSUMERS ON THE VIRTUAL WAITLIST OPERATION 209 a given healthcare service consumer requesting to be placed on the virtual open appointment wait list provides process for providing real time appointment rescheduling with patient virtual open appointment wait list data.

In one embodiment, the patient virtual open appointment wait list data provided at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 includes, but not limited to, the healthcare service consumer's name and/or other identification such as a Social Security number, insurance number, or any other number and/or code uniquely identifying the healthcare service consumer.

In one embodiment, the patient virtual open appointment wait list data provided at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 includes, but is not limited to, contact information for the healthcare service consumer including, but not limited to, one or more of the following: mobile device contact information, such as a cell phone or pager number; an e-mail address; a home telephone number; an address; a work telephone number; or any other information required to contact the healthcare service consumer by any means and/or procedure.

In one embodiment, the patient virtual open appointment wait list data provided at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 includes, but is not limited to, the name and/or identification for healthcare service provider, or providers, desired to be seen and/or a specialist type desired.

In one embodiment, the patient virtual open appointment wait list data provided at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 includes, but is not limited to, the type of appointment desired and/or the type of service desired, such physical, X-ray, blood work, urine analysis, etc.

In one embodiment, the patient virtual open appointment wait list data provided at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 includes, but is not limited to, a time frame for the desired appointment, such as "in the next two weeks", or excluding times when the healthcare service consumer will not be available.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 all, or part of, the patient virtual open appointment wait list data associated with a given healthcare service consumer is obtained from the healthcare service consumer directly.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 all, or part of, the patient virtual open appointment wait list data associated with a given healthcare service consumer is obtained from a mobile computing device associated with the healthcare service consumer.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 all, or part of, the patient virtual open appointment wait list data associated with a given healthcare service consumer is obtained from a computing system implemented data management system associated with the healthcare service consumer and/or the healthcare service provider, such as computing system implemented data management system 190 of FIG. 1.

Returning to FIG. 2, in one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 all, or part of, the patient virtual open appointment wait list data associated with a given healthcare service consumer is obtained from a computing system implemented healthcare management system associated with the healthcare service consumer and/or the healthcare service provider.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 process for providing real time appointment rescheduling 200 obtains provider virtual open appointment wait list data.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 the provider virtual open appointment wait list data includes, but is not limited to, an assigned virtual open appointment wait list data identification code indicating the position on the virtual open appointment wait list assigned to the healthcare service consumer. In one embodiment, the assigned virtual open appointment wait list data identification code helps ensure that newly available appointment slots are offered to eligible healthcare service consumers in a systematic order, such as a first come, first served, order.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 the provider virtual open appointment wait list data includes, but is not limited to, an approximate appointment length associated with the type of appointment indicated in the patient virtual open appointment wait list data. In this instance, the healthcare service provider estimates how long an appointment a given healthcare service consumer requires for the type of service indicated in the patient virtual open appointment wait list data.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 the provider virtual open appointment wait list data includes, but is not limited to, and data indicating the currently assigned appointment for the healthcare service consumer.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, all, or part of, the provider virtual open appointment wait list data is entered by the healthcare service provider and/or an employee of the healthcare service provider into a computing system implementing, and/or other wise associated with, process for providing real time appointment rescheduling 200 using a user interface device, as discussed herein, and/or known in the art at the time of filing, and/or as developed after the time of filing.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, all, or part of, the provider virtual open appointment wait list data is obtained from a computing system associated with the healthcare service provider, such as computing system 100 of FIG. 1.

Returning to FIG. 2, in one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, all, or part of, the provider virtual open appointment wait list data is obtained from a computing system implemented data management system associated with the healthcare service provider, such as computing system implemented appointment management system 180 of FIG. 1.

Returning to FIG. 2, in one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, all, or part of, the provider virtual open appointment wait list data is obtained from a computing system implemented healthcare management system associated with the healthcare service provider.

In one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, once the patient and provider virtual open appointment wait list data, herein collectively referred to as "virtual open appointment wait list data", is obtained, the data is stored, in whole, or in part, in a database, such as databases 170, 171, or 172 of FIG. 1 maintained by, accessible by, owned by, or otherwise related to: process for providing real time appointment rescheduling 200, and/or a provider of process for providing real time appointment rescheduling 200; a computing system implemented data management system, and/or a provider of a computing system implemented data management system; or any other party, by any one of the numerous mechanisms known to those of skill in the art.

For instance, in one embodiment, at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 the virtual open appointment wait list data is stored, in whole, or in part, in a memory system, such as memory systems 103 and 153 or server memory system 123, or databases 170, 171, and/or 172, of FIG. 1, or in a cache memory, such as cache memories 103A/153A of FIG. 1, or in any main memory or mass memory, associated with a computing system, such as computing systems 100 or 150 described above. In one embodiment, the data, in whole, or in part, is stored in any computing system and/or server system, such as computing systems 100 or 150 or server system 120, or other device, in another location, or on/in a computer readable medium, and/or any other computer program product, as defined herein. In one embodiment, the data, in whole, or in part, is stored in a database, such as one or more of databases 170, 171 and/or 172 of FIG. 1. In one embodiment, the data, in whole, or in part, is stored on a webpage, in a web-based system or on a public network such as the Internet.

In one embodiment, once the virtual waitlist data required to place a healthcare service provider on the virtual open appointment wait list is provided to process for providing real time appointment rescheduling 200 at OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 and, in one embodiment, is stored, process flow proceeds to AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 an appointment becomes available and the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a healthcare service consumer on the waitlist whose patient and provider virtual open appointment wait list data is consistent with the newly available appointment, i.e., who is a good match for the newly available appointment.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 an appointment becomes available due to a cancellation, or unused healthcare service provider scheduled break time, or unused healthcare service provider allotted emergency visit time, or for any other reason that an appointment could become unexpectedly available.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer that is next on the virtual open appointment wait list, and whose patient and provider virtual open appointment wait list data is consistent with the newly available appointment.

For instance, in one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer having an assigned virtual open appointment wait list data identification code indicating he or she is in the first, or next, position on the virtual open appointment wait list. In this way potential healthcare service consumers can be offered the newly available appointment in an order reflective of the time they have waited for an appointment, i.e., on a first come, first served, basis.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer on the virtual open appointment wait list that has indicated a desire to see the specific healthcare service provider associated with the newly available appointment. In this way a healthcare service consumer is provided the opportunity to accept only appointments that become available with a specific healthcare service provider.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer on the virtual open appointment wait list desiring an appointment having an approximate appointment length equal to the estimated appointment length associated with the newly available appointment. In this way healthcare service consumers are only offered the newly available appointments that meet their time needs. For instance, healthcare service consumers requiring a 60 minute appointment are not offered 30 minute appointment slots.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer on the virtual open appointment wait list desiring an appointment in a time frame consistent with the newly available appointment. In this instance, the healthcare service consumer is not offered a newly available appointment that they cannot make, such as an appointment that becomes available when they are out-of-town, or must work.

In one embodiment, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, when an appointment becomes available, the patient and provider virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a first healthcare service consumer on the virtual open appointment wait list desiring a type of appointment consistent with the newly available appointment. In this case, the healthcare service consumer is offered newly available appointments that meet their needs. For instance, a given healthcare service provider may only perform annual physicals on Tuesdays. In this case, a healthcare service consumer needing a physical will only be offered newly available appointments on Tuesdays.

In one embodiment, one or more of the healthcare service consumers on the virtual open appointment wait list have mobile computing systems, such as a cellular phone, that include global positioning satellite capability, or a similar positioning capability. In these instances, and particularly when an appointment becomes available on very short notice, at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, the healthcare service consumers closet to the healthcare service provider's office when the appointment becomes available are offered newly available appointments first.

In one embodiment, once an appointment becomes available and the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched to find a healthcare service consumer on the waitlist whose patient and provider virtual open appointment wait list data is consistent with the newly available appointment at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, process flow proceeds to SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213.

In one embodiment, at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 the first healthcare service consumer identified at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 is contacted in accordance with the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 and the first healthcare service consumer is given a designated period of time to respond and accept the newly available appointment.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via a mobile computing system such as, but not limited to: a cellular phone; a pager; a text messaging device; a PDA; a car phone; etc.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via any computing system, as discussed herein, and/or known in the art at the time of filing, and/or as developed after the time of filing.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via traditional telephone service.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via postal service.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via a website and/or web-based function, as discussed herein, and/or known in the art at the time of filing, and/or as developed after the time of filing.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 by linking to, and/or accessing, one or more databases, and/or computing systems, and/or websites associated with one or more healthcare service providers, and/or one or more healthcare insurance plan administrators, as discussed herein, and/or known in the art at the time of filing, and/or as developed after the time of filing.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via a computer program product as defined herein.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 through a network of computing systems and/or server systems, as discussed herein, and/or known in the art at the time of filing, and/or as developed after the time of filing, that is comprised of multiple different computers, wireless devices, cellular telephones, digital telephones, two-way pagers, personal digital assistants, server computers, or any desired combination of these devices, that are interconnected using any network, as discussed herein, and/or known in the art at the time of filing, and/or as developed after the time of filing.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 via e-mail and/or through text messaging.

In one embodiment, the first healthcare service consumer is contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 using any method, apparatus, process or mechanism for transferring data, images, screen displays, and/or text from one or more devices, computing systems, server systems, databases, web site/web functions and/or any devices to one or more other devices, computing systems, server systems, databases, web site/web functions and/or any devices having a data storage and/or display capability, whether known at the time of filing or as thereafter developed.

In one embodiment, at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 when the first healthcare service consumer is contacted, the first healthcare service consumer is given a designated period of time to respond and accept the newly available appointment. In one embodiment, the designated period of time is determined based how much time is available between when the first healthcare service consumer is being contacted and newly available appointment time. For instance, in the case of a same day newly available appointment time, the designated period of time to respond and accept may be a matter of minutes or hours. On the other hand, in the case of a newly available appointment time weeks in the future, the designated period of time to respond and accept may be a matter of days.

In one embodiment, once the first healthcare service consumer identified at AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 is contacted in accordance with the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 and the first healthcare service consumer is given a designated period of time to respond and accept the newly available appointment at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213, process flow proceeds to WAIT A DESIGNATED PERIOD OF TIME FOR A RESPONSE FROM THE FIRST HEALTHCARE SERVICE CONSUMER OPERATION 215.

In one embodiment, at WAIT A DESIGNATED PERIOD OF TIME FOR A RESPONSE FROM THE FIRST HEALTHCARE SERVICE CONSUMER OPERATION 215 the first healthcare service consumer contacted at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 is given the designated period of time to respond and accept the newly available appointment of AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 as set forth in the data sent at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213.

In one embodiment, if the first healthcare service consumer responds and accepts the newly available appointment of AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211 within the designated period of time to respond and accept, the first healthcare service consumer is given the newly available appointment. In one embodiment, if the first healthcare service consumer had a previously scheduled appointment from RECEIVE A REQUEST FROM ONE OR MORE HEALTHCARE SERVICE CONSUMERS TO BE PLACED ON THE VIRTUAL WAIT LIST OPERATION 207, and as indicated by the data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209, then, when the first healthcare service consumer is given the newly available appointment, the previously scheduled appointment becomes a newly available appointment, and process for providing real time appointment rescheduling 200 is implemented for this newly available appointment.

On the other hand, in one embodiment, if the first healthcare service consumer actively declines the newly available appointment of AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, or fails to respond within the designated period of time of SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213 and accept, the newly available appointment of AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, process flow proceeds to AFTER THE DESIGNATED PERIOD HAS PASSED, SEND DATA TO A SECOND HEALTHCARE SERVICE CONSUMER THAT IS NEXT ON THE VIRTUAL WAITLIST INFORMING THE SECOND HEALTHCARE SERVICE CONSUMER OF THE AVAILABLE APPOINTMENT OPERATION 217.

In one embodiment, if the first healthcare service consumer actively declines the newly available appointment, or if the first healthcare service consumer fails to respond within the designated period of time to respond and accept, after the designated period of time has passed, at AFTER THE DESIGNATED PERIOD HAS PASSED, SEND DATA TO A SECOND HEALTHCARE SERVICE CONSUMER THAT IS NEXT ON THE VIRTUAL WAITLIST INFORMING THE SECOND HEALTHCARE SERVICE CONSUMER OF THE AVAILABLE APPOINTMENT OPERATION 217 the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 is searched again to find a second healthcare service consumer that is next, after the first healthcare service consumer, on the virtual open appointment wait list, and whose patient and provider virtual open appointment wait list data is consistent with the newly available appointment.

In one embodiment, at AFTER THE DESIGNATED PERIOD HAS PASSED, SEND DATA TO A SECOND HEALTHCARE SERVICE CONSUMER THAT IS NEXT ON THE VIRTUAL WAITLIST INFORMING THE SECOND HEALTHCARE SERVICE CONSUMER OF THE AVAILABLE APPOINTMENT OPERATION 217 the second healthcare service consumer is contacted in accordance with the virtual open appointment wait list data of OBTAIN VIRTUAL WAITLIST DATA FOR THE ONE OR MORE HEALTHCARE SERVICE CONSUMERS AND PLACE THE ONE OR MORE HEALTHCARE SERVICE CONSUMERS ON THE VIRTUAL WAITLIST OPERATION 209 and the second healthcare service consumer is given a designated period of time to respond and accept, or decline, the newly available appointment in a manner similar to that employed, and using any of the means discussed, to contact the first healthcare service consumer at SEND DATA TO A FIRST HEALTHCARE SERVICE CONSUMER THAT IS NEXT ON THE VIRTUAL WAITLIST INFORMING THE FIRST HEALTHCARE SERVICE CONSUMER OF THE AVAILABLE APPOINTMENT OPERATION 213.

In one embodiment, this process is repeated automatically until the newly available appointment is accepted by one of the healthcare service consumers of RECEIVE A REQUEST FROM ONE OR MORE HEALTHCARE SERVICE CONSUMERS TO BE PLACED ON THE VIRTUAL WAIT LIST OPERATION 207 on the virtual open appointment wait list of PROVIDE A VIRTUAL WAIT LIST OPERATION 205.

In one embodiment, if the newly available appointment is not accepted by one of the healthcare service consumers of RECEIVE A REQUEST FROM ONE OR MORE HEALTHCARE SERVICE CONSUMERS TO BE PLACED ON THE VIRTUAL WAIT LIST OPERATION 207 on the virtual open appointment wait list of PROVIDE A VIRTUAL WAIT LIST OPERATION 205 during a first pass through the healthcare service consumers on the virtual open appointment wait list of PROVIDE A VIRTUAL WAIT LIST OPERATION 205, process for providing real time appointment rescheduling begins again with the first healthcare service consumer on the virtual open appointment wait list of PROVIDE A VIRTUAL WAIT LIST OPERATION 205 that did not actively decline the newly available appointment, and the process is repeated in a loop fashion automatically until either the newly available appointment is either actively declined by each of the healthcare service consumers of RECEIVE A REQUEST FROM ONE OR MORE HEALTHCARE SERVICE CONSUMERS TO BE PLACED ON THE VIRTUAL WAIT LIST OPERATION 207 on the virtual open appointment wait list of PROVIDE A VIRTUAL WAIT LIST OPERATION 205 or is accepted by one of the healthcare service consumers of RECEIVE A REQUEST FROM ONE OR MORE HEALTHCARE SERVICE CONSUMERS TO BE PLACED ON THE VIRTUAL WAIT LIST OPERATION 207 on the virtual open appointment wait list of PROVIDE A VIRTUAL WAIT LIST OPERATION 205.

In one embodiment, once one of the healthcare service consumers of RECEIVE A REQUEST FROM ONE OR MORE HEALTHCARE SERVICE CONSUMERS TO BE PLACED ON THE VIRTUAL WAIT LIST OPERATION 207 on the virtual open appointment wait list of PROVIDE A VIRTUAL WAIT LIST OPERATION 205 accepts the newly available appointment of AN APPOINTMENT BECOMES AVAILABLE THAT IS CONSISTENT WITH THE DATA ASSOCIATED WITH THE ONE OR MORE HEALTHCARE SERVICE CONSUMERS OPERATION 211, process flow proceeds to EXIT OPERATION 230. In one embodiment, at EXIT OPERATION 230, process for providing real time appointment rescheduling 200 is exited to await new data.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Using process for providing real time appointment rescheduling 200, healthcare service providers can backfill cancelled appointments, or appointments that have otherwise become available, in a systematic and automatic manner without using significant employee time and energy. Consequently, using process for providing real time appointment rescheduling 200, healthcare service providers can backfill cancelled appointments, or appointments that have otherwise become available, in fair efficient manner that benefits both healthcare service providers and their healthcare service consumers.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "receiving", "sending", "obtaining", "using", "identifying", "providing", "aggregating", "storing", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus, means, or system for performing the operations described herein. This apparatus, means, or system may be specifically constructed for the required purposes, or the apparatus, means, or system can comprise a general purpose system selectively activated or configured/reconfigured by a computer program stored via a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of networks, are defined herein, operating over numerous topologies.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

In the discussion above, certain aspects of various embodiments include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Therefore, numerous variations, whether explicitly provided for by the specification or implied by the specification or not, may be implemented by one of skill in the art in view of this disclosure.

What is claimed is:

1. A system for providing real time appointment rescheduling comprising:
   one or more computing processors; and
   one or more memories coupled to the one or more processors, the one or more memories having stored therein computing processor executable instructions which when executed by the one or more computing processors perform a process comprising:
   obtaining access to one or more computing system implemented appointment management systems, the one or more computing system implemented service appointment management systems being used by one or more service providers;
   providing a virtual open appointment waitlist for one or more service appointments scheduled through one or more of the one or more computing system implemented appointment management systems;
   receiving a request from one or more service consumers to be placed on the virtual open appointment waitlist for one or more service appointments scheduled through one or more of the one or more computing system implemented appointment management systems;
   obtaining virtual open appointment waitlist data associated each of the one or more service consumers requesting to be placed on the virtual open appointment waitlist, the virtual open appointment waitlist data including mobile device contact information for each of the one or more service consumers, and a position on the virtual open appointment waitlist for each of the one or more service consumers relative to each of the other one or more service consumers on the virtual open appointment waitlist, the mobile devices associated with each of the one or more service consumers including a location indicating capability, the virtual open appointment waitlist data further including one or more dates and times that the service consumer is not available for an appointment;
   when a service appointment becomes newly available, analyzing the virtual open appointment waitlist data from the one or more service consumers requesting to be placed on the virtual open appointment waitlist, the analyzing including determining a location of the one or more service consumers, the analysis excluding from consideration any service consumer that previously indicated a lack of availability for a time or date of the service appointment, the analyzing primarily to determine a first service consumer in the highest relative position on the virtual open appointment waitlist whose associated virtual open appointment waitlist data is consistent with the newly available service appointment;
   automatically contacting the first service consumer on the virtual open appointment waitlist using the first service consumer's mobile device contact information and sending the first service consumer on the virtual open appointment waitlist data indicating the newly available service appointment and data indicating a designated period of time within which the first service consumer on the virtual open appointment waitlist must accept the newly available service appointment;
   after the designated period of time, if the first service consumer on the virtual open appointment waitlist has not accepted the newly available service appointment, analyzing the virtual open appointment waitlist data from the one or more service consumers requesting to be placed on the virtual open appointment waitlist to determine a second service consumer in the highest relative position on the virtual open appointment waitlist, after the first service consumer, whose associated virtual open appointment waitlist data is consistent with the newly available service appointment; and
   automatically contacting the second service consumer on the virtual open appointment waitlist using the second service consumer's mobile device contact information and sending the second service consumer on the virtual open appointment waitlist data indicating the newly available service appointment and data indicating a designated period of time within which the second service consumer on the virtual open appointment waitlist must accept the newly available service appointment.

2. The computing system for providing real time appointment rescheduling of claim 1, wherein;
   at least part of the virtual open appointment waitlist data associated each of the one or more service consumers requesting to be placed on the virtual open appointment waitlist is chosen from the group of virtual open appointment waitlist data consisting of:
   the service consumer's name or other identification data;
   contact information for the service consumer;
   the name or identification for the service provider, or providers, the service consumer desires to see;
   the type of appointment desired;
   a time frame for the desired appointment;
   an assigned virtual open appointment wait list data identification code indicating the position on the virtual open appointment wait list assigned to the service consumer;
   approximate appointment length associated with the type of appointment desired by the service consumer; and
   data indicating any currently assigned appointment for the service consumer.

3. The system for providing real time appointment rescheduling of claim 1, wherein;
   analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the service provider associated with the newly available service appointment is the same as the service provider the service consumer desires to see.

4. The system for providing real time appointment rescheduling of claim 1, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the type of appointment associated with the newly available service appointment is the same as the type of service appointment the service consumer desires.

5. The system for providing real time appointment rescheduling of claim 1, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the time associated with the newly available appointment is consistent with a time frame for the desired appointment indicated by the service consumer.

6. The system for providing real time appointment rescheduling of claim 1, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the approximate appointment length newly available appointment is consistent with the approximate appointment length associated with the type of service appointment desired by the service consumer.

7. A system for providing real time healthcare service appointment rescheduling comprising:

one or more computing processors; and
one or more memories coupled to the one or more processors, the one or more memories having stored therein computing processor executable instructions which when executed by the one or more computing processors perform a process comprising:
obtaining access to one or more computing system implemented healthcare service appointment management systems, the one or more computing system implemented healthcare service appointment management systems being used by one or more healthcare service providers;
providing a virtual open appointment waitlist for one or more healthcare service appointments scheduled through one or more of the one or more computing system implemented healthcare service appointment management systems;
receiving a request from one or more healthcare service consumers to be placed on the virtual open appointment waitlist for one or more healthcare service appointments with the healthcare service provider scheduled through one or more of the one or more computing system implemented a healthcare service appointment management systems;
obtaining virtual open appointment waitlist data associated each of the one or more healthcare service consumers requesting to be placed on the virtual open appointment waitlist, the virtual open appointment waitlist data including mobile device contact information for each of the one or more healthcare service consumers and a position on the virtual open appointment waitlist for each of the one or more healthcare service consumers relative to each of the other one or more healthcare service consumers on the virtual open appointment waitlist, the mobile devices associated with each of the one or more healthcare service consumers including a location indicating capability, the virtual open appointment waitlist data further including one or more dates and times that the healthcare service consumer is not available for an appointment;
when a healthcare service appointment becomes newly available, analyzing the virtual open appointment waitlist data from the one or more healthcare service consumers requesting to be placed on the virtual open appointment waitlist the analyzing including determining a location of the one or more healthcare service consumers, the analysis excluding from consideration any healthcare service consumer that previously indicated a lack of availability for a time or date of the healthcare service appointment, the analyzing primarily to determine a first healthcare service consumer in the highest relative position on the virtual open appointment waitlist whose associated virtual open appointment waitlist data is consistent with the newly available appointment;
automatically contacting the first healthcare service consumer on the virtual open appointment waitlist using the first healthcare service consumer's mobile device contact information and sending the first healthcare service consumer data indicating the newly available healthcare service appointment and data indicating a designated period of time within which the first healthcare service consumer must accept the newly available healthcare service appointment;
after the designated period of time, if the first healthcare service consumer on the virtual open appointment waitlist has not accepted the newly available healthcare service appointment, analyzing the virtual open appointment waitlist data from the one or more healthcare service consumers requesting to be placed on the virtual open appointment waitlist to determine a second healthcare service consumer in the highest relative position on the virtual open appointment waitlist, after the first healthcare service consumer, whose associated virtual open appointment waitlist data is consistent with the newly available healthcare service appointment; and
automatically contacting the second healthcare service consumer using the second healthcare service consumer's mobile device contact information and sending the second healthcare service consumer data indicating the newly available healthcare service appointment and data indicating a designated period of time within which the second healthcare service consumer must accept the newly available healthcare service appointment.

8. The system for providing real time healthcare service appointment rescheduling of claim 7, wherein;
at least part of the virtual open appointment waitlist data associated each of the one or more healthcare service consumers requesting to be placed on the virtual open appointment waitlist is chosen from the group of virtual open appointment waitlist data consisting of:
the healthcare service consumer's name or other identification data;
the name or identification for the healthcare service provider, or healthcare providers, the healthcare service consumer desires to see;
the type of healthcare service appointment desired;
a time frame for the desired appointment;
an assigned virtual open appointment wait list data identification code indicating the position on the virtual open appointment wait list assigned to the healthcare service consumer;
approximate appointment length associated with the type of appointment desired by the healthcare service consumer; and
data indicating any currently assigned appointment for the healthcare service consumer.

9. The system for providing real time healthcare service appointment rescheduling of claim 7, wherein;
analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the healthcare service provider associated with the newly available healthcare service appointment is the same as the healthcare service provider the healthcare service consumer desires to see.

10. The system for providing real time healthcare service appointment rescheduling of claim 7, wherein;
analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated appointment waitlist data from the one or more healthcare service consumers to ensure the type of healthcare service appointment associated with the newly available healthcare service appointment is the same as the type of healthcare service appointment the healthcare service consumer desires.

11. The system for providing real time healthcare service appointment rescheduling of claim 7, wherein;
analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the time associated with the newly available healthcare appointment is consistent with a time frame for the desired healthcare service appointment indicated by the healthcare service consumer.

12. The system for providing real time healthcare service appointment rescheduling of claim 7, wherein;
analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the approximate appointment length newly available healthcare service appointment is consistent with the approximate appointment length associated with the type of healthcare service appointment desired by the service consumer.

13. A computer program product for providing a process for providing real time appointment rescheduling comprising:
a nontransitory computer readable medium;
and computer program code, encoded on the computer readable medium, comprising computer readable instructions for:
obtaining access to one or more computing system implemented appointment management systems, the one or more computing system implemented service appointment management systems being used by one or more service providers;
providing a virtual open appointment waitlist for one or more service appointments scheduled through one or more of the one or more computing system implemented appointment management systems;
receiving a request from one or more service consumers to be placed on the virtual open appointment waitlist for one or more service appointments scheduled through one or more of the one or more computing system implemented appointment management systems;
obtaining virtual open appointment waitlist data associated each of the one or more service consumers requesting to be placed on the virtual open appointment waitlist, the virtual open appointment waitlist data including mobile device contact information for each of the one or more service consumers, and a position on the virtual open appointment waitlist for each of the one or more service consumers relative to each of the other one or more service consumers on the virtual open appointment waitlist, the mobile devices associated with each of the one or more service consumers including a location indicating capability, the virtual open appointment waitlist data further including one or more dates and times that the service consumer is not available for an appointment;
when a service appointment becomes newly available, analyzing the virtual open appointment waitlist data from the one or more service consumers requesting to be placed on the virtual open appointment waitlist, the analyzing including determining a location of the one or more service consumers, the analysis excluding from consideration any service consumer that previously indicated a lack of availability for a time or date of the service appointment, the analyzing primarily to determine a first service consumer in the highest relative position on the virtual open appointment waitlist whose associated virtual open appointment waitlist data is consistent with the newly available service appointment;

automatically contacting the first service consumer on the virtual open appointment waitlist using the first service consumer's mobile device contact information and sending the first service consumer on the virtual open appointment waitlist data indicating the newly available service appointment and data indicating a designated period of time within which the first service consumer on the virtual open appointment waitlist must accept the newly available service appointment;

after the designated period of time, if the first service consumer on the virtual open appointment waitlist has not accepted the newly available service appointment, analyzing the virtual open appointment waitlist data from the one or more service consumers requesting to be placed on the virtual open appointment waitlist to determine a second service consumer in the highest relative position on the virtual open appointment waitlist, after the first service consumer, whose associated virtual open appointment waitlist data is consistent with the newly available service appointment; and automatically contacting the second service consumer on the virtual open appointment waitlist using the second service consumer's mobile device contact information and sending the second service consumer on the virtual open appointment waitlist data indicating the newly available service appointment and data indicating a designated period of time within which the second service consumer on the virtual open appointment waitlist must accept the newly available service appointment.

14. The computer program product for providing a process for providing real time appointment rescheduling of claim 13, wherein;

at least part of the virtual open appointment waitlist data associated each of the one or more service consumers requesting to be placed on the virtual open appointment waitlist is chosen from the group of virtual open appointment waitlist data consisting of:

the service consumer's name or other identification data;
contact information for the service consumer;
the name or identification for the service provider, or providers, the service consumer desires to see;
the type of appointment desired;
a time frame for the desired appointment;
an assigned virtual open appointment wait list data identification code indicating the position on the virtual open appointment wait list assigned to the service consumer;
approximate appointment length associated with the type of appointment desired by the service consumer; and
data indicating any currently assigned appointment for the service consumer.

15. The computer program product for providing a process for providing real time appointment rescheduling of claim 13, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the service provider associated with the newly available service appointment is the same as the service provider the service consumer desires to see.

16. The computer program product for providing a process for providing real time appointment rescheduling of claim 13, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the type of appointment associated with the newly available service appointment is the same as the type of service appointment the service consumer desires.

17. The computer program product for providing a process for providing real time appointment rescheduling of claim 13, wherein;

analyzing the virtual open appointment waitlist data from the one or more service consumers requesting to be placed on the virtual open appointment waitlist to determine a service consumer on the virtual open appointment waitlist whose associated virtual open appointment waitlist data is consistent with the newly available service appointment comprises comparing data associated with the newly available service appointment with the virtual open appointment waitlist data from the one or more service consumers to ensure the time associated with the newly available appointment is consistent with a time frame for the desired appointment indicated by the service consumer.

18. The computer program product for providing a process for providing real time appointment rescheduling of claim 13, wherein;

analyzing the virtual open appointment waitlist data from the one or more service consumers requesting to be placed on the virtual open appointment waitlist to associated virtual open appointment waitlist data is consistent with the newly available service appointment comprises comparing data associated with the newly available service appointment with the virtual open appointment waitlist data from the one or more service consumers to ensure the approximate appointment length newly available appointment is consistent with the approximate appointment length associated with the type of service appointment desired by the service consumer.

19. A computer program product for providing a process for providing real time healthcare service appointment rescheduling comprising:

a non-transitory computer readable medium;
and computer program code, encoded on the computer readable medium, comprising computer readable instructions for:
obtaining access to one or more computing system implemented healthcare service appointment management systems, the one or more computing system implemented healthcare service appointment management systems being used by one or more healthcare service providers;
providing a virtual open appointment waitlist for one or more healthcare service appointments scheduled through one or more of the one or more computing system implemented healthcare service appointment management systems;

receiving a request from one or more healthcare service consumers to be placed on the virtual open appointment waitlist for one or more healthcare service appointments with the healthcare service provider scheduled through one or more of the one or more computing system implemented a healthcare service appointment management systems;

obtaining virtual open appointment waitlist data associated each of the one or more healthcare service consumers requesting to be placed on the virtual open appointment waitlist, the virtual open appointment waitlist data including mobile device contact information for each of the one or more healthcare service consumers and a position on the virtual open appointment waitlist for each of the one or more healthcare service consumers relative to each of the other one or more healthcare service consumers on the virtual open appointment waitlist, the mobile devices associated with each of the one or more healthcare service consumers including a location indicating capability, the virtual open appointment waitlist data further including one or more dates and times that the healthcare service consumer is not available for an appointment;

when a healthcare service appointment becomes newly available, analyzing the virtual open appointment waitlist data from the one or more healthcare service consumers requesting to be placed on the virtual open appointment waitlist the analyzing including determining a location of the one or more healthcare service consumers, the analysis excluding from consideration any healthcare service consumer that previously indicated a lack of availability for a time or date of the healthcare service appointment, the analyzing primarily to determine a first healthcare service consumer in the highest relative position on the virtual open appointment waitlist whose associated virtual open appointment waitlist data is consistent with the newly available appointment;

automatically contacting the first healthcare service consumer on the virtual open appointment waitlist using the first healthcare service consumer's mobile device contact information and sending the first healthcare service consumer data indicating the newly available healthcare service appointment and data indicating a designated period of time within which the first healthcare service consumer must accept the newly available healthcare service appointment;

after the designated period of time, if the first healthcare service consumer on the virtual open appointment waitlist has not accepted the newly available healthcare service appointment, analyzing the virtual open appointment waitlist data from the one or more healthcare service consumers requesting to be placed on the virtual open appointment waitlist to determine a second healthcare service consumer in the highest relative position on the virtual open appointment waitlist, after the first healthcare service consumer, whose associated virtual open appointment waitlist data is consistent with the newly available healthcare service appointment; and automatically contacting the second healthcare service consumer using the second healthcare service consumer's mobile device contact information and sending the second healthcare service consumer data indicating the newly available healthcare service appointment and data indicating a designated period of time within which the second healthcare service consumer must accept the newly available healthcare service appointment.

20. The computer program product for providing a process for providing real time healthcare service appointment rescheduling of claim 19, wherein;

at least part of the virtual open appointment waitlist data associated each of the one or more healthcare service consumers requesting to be placed on the virtual open appointment waitlist is chosen from the group of virtual open appointment waitlist data consisting of:

the healthcare service consumer's name or other identification data;

the name or identification for the healthcare service provider, or healthcare providers, the healthcare service consumer desires to see;

the type of healthcare service appointment desired;

a time frame for the desired appointment;

an assigned virtual open appointment wait list data identification code indicating the position on the virtual open appointment wait list assigned to the healthcare service consumer;

approximate appointment length associated with the type of appointment desired by the healthcare service consumer; and data indicating any currently assigned appointment for the healthcare service consumer.

21. The computer program product for providing a process for providing real time healthcare service appointment rescheduling of claim 19, wherein;

analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the healthcare service provider associated with the newly available healthcare service appointment is the same as the healthcare service provider the healthcare service consumer desires to see.

22. The computer program product for providing a process for providing real time healthcare service appointment rescheduling of claim 19, wherein;

analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the type of healthcare service appointment associated with the newly available healthcare service appointment is the same as the type of healthcare service appointment the healthcare service consumer desires.

23. The computer program product for providing a process for providing real time healthcare service appointment rescheduling of claim 19, wherein;

analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the time associated with the newly available healthcare appointment is consistent with a time frame for the desired healthcare service appointment indicated by the healthcare service consumer.

24. The computer program product for providing a process for providing real time healthcare service appointment rescheduling of claim 19, wherein;

analyzing the virtual open appointment waitlist data from the one or more healthcare service consumers requesting to be placed on the virtual open appointment waitlist to determine a healthcare service consumer on the virtual open appointment waitlist whose associated virtual open appointment waitlist data is consistent with the newly available healthcare service appointment comprises comparing data associated with the newly available healthcare service appointment with the virtual open appointment waitlist data from the one or more healthcare service consumers to ensure the approximate appointment length newly available healthcare service appointment is consistent with the approximate appointment length associated with the type of healthcare service appointment desired by the service consumer.

25. A system for providing real time appointment rescheduling comprising:

one or more computing system implemented appointment management systems;

one or more mobile devices, the one or more mobile devices being associated with one or more healthcare service consumers; and a processor for executing at least part of a process for providing real time appointment rescheduling, the process for providing real time appointment rescheduling comprising:

obtaining access to the one or more computing system implemented appointment management systems, the one or more computing system implemented service appointment management systems being used by one or more service providers;

providing a virtual open appointment waitlist for one or more service appointments scheduled through one or more of the one or more computing system implemented appointment management systems;

receiving a request from one or more service consumers to be placed on the virtual open appointment waitlist for one or more service appointments scheduled through one or more of the one or more computing system implemented appointment management systems;

obtaining virtual open appointment waitlist data associated each of the one or more service consumers requesting to be placed on the virtual open appointment waitlist, the virtual open appointment waitlist data including mobile device contact information for each of the one or more service consumers, and a position on the virtual open appointment waitlist for each of the one or more service consumers relative to each of the other one or more service consumers on the virtual open appointment waitlist, the mobile devices associated with each of the one or more service consumers including a location indicating capability, the virtual open appointment waitlist data further including one or more dates and times that the service consumer is not available for an appointment;

when a service appointment becomes newly available, analyzing the virtual open appointment waitlist data from the one or more service consumers requesting to be placed on the virtual open appointment waitlist, the analyzing including determining a location of the one or more service consumers, the analysis excluding from consideration any service consumer that previously indicated a lack of availability for a time or date of the service appointment, the analyzing primarily to determine a first service consumer in the highest relative position on the virtual open appointment waitlist whose associated virtual open appointment waitlist data is consistent with the newly available service appointment;

automatically contacting the first service consumer on the virtual open appointment waitlist using the first service consumer's mobile device contact information and sending the first service consumer on the virtual open appointment waitlist data indicating the newly available service appointment and data indicating a designated period of time within which the first service consumer on the virtual open appointment waitlist must accept the newly available service appointment;

after the designated period of time, if the first service consumer on the virtual open appointment waitlist has not accepted the newly available service appointment, analyzing the virtual open appointment waitlist data from the one or more service consumers requesting to be placed on the virtual open appointment waitlist to determine a second service consumer in the highest relative position on the virtual open appointment waitlist, after the first service consumer, whose associated virtual open appointment waitlist data is consistent with the newly available service appointment; and automatically contacting the second service consumer on the virtual open appointment waitlist using the second service consumer's mobile device contact information and sending the second service consumer on the virtual open appointment waitlist data indicating the newly available service appointment and data indicating a designated period of time within which the second service consumer on the virtual open appointment waitlist must accept the newly available service appointment.

26. A system for providing real time healthcare service appointment rescheduling comprising:

one or more computing system implemented healthcare service appointment management systems, the one or more computing system implemented healthcare service appointment management systems being used by one or more healthcare service providers;

one or more mobile devices, the one or more mobile devices being associated with one or more healthcare service consumers; and a processor for executing at least part of a process for providing real time healthcare service appointment rescheduling, the process for providing real time healthcare service appointment rescheduling comprising:

obtaining access to the one or more computing system implemented healthcare service appointment management systems;

providing a virtual open appointment waitlist for one or more healthcare service appointments scheduled through one or more of the one or more computing system implemented healthcare service appointment management systems;

receiving a request from one or more healthcare service consumers to be placed on the virtual open appointment waitlist for one or more healthcare service appointments with the healthcare service provider scheduled through one or more of the one or more computing system implemented a healthcare service appointment management systems;

obtaining virtual open appointment waitlist data associated each of the one or more healthcare service consumers requesting to be placed on the virtual open appointment waitlist, the virtual open appointment waitlist data including contact information for each of the one or more mobile devices associated with the one or more healthcare service consumers and a position on the virtual open appointment waitlist for each of the one or more healthcare service consumers relative to each of the other one or more healthcare service consumers on the virtual open appointment waitlist, the mobile devices associated with each of the one or more healthcare service consumers including a location indicating capability, the virtual open appointment waitlist data further including one or more dates and times that the healthcare service consumer is not available for an appointment;

when a healthcare service appointment becomes newly available, analyzing the virtual open appointment waitlist data from the one or more healthcare service consumers requesting to be placed on the virtual open appointment waitlist the analyzing including determining a location of the one or more healthcare service consumers, the analysis excluding from consideration any healthcare service consumer that previously indicated a lack of availability for a time or date of the healthcare service appointment, the analyzing primarily to determine a first healthcare service consumer in the highest relative position on the virtual open appointment waitlist whose associated virtual open appointment waitlist data is consistent with the newly available appointment;

automatically contacting the first healthcare service consumer on the virtual open appointment waitlist using the first healthcare service consumer's mobile device contact information and sending the first healthcare service consumer data indicating the newly available healthcare service appointment and data indicating a designated period of time within which the first healthcare service consumer must accept the newly available healthcare service appointment;

after the designated period of time, if the first healthcare service consumer on the virtual open appointment waitlist has not accepted the newly available healthcare service appointment, analyzing the virtual open appointment waitlist data from the one or more healthcare service consumers requesting to be placed on the virtual open appointment waitlist to determine a second healthcare service consumer in the highest relative position on the virtual open appointment waitlist, after the first healthcare service consumer, whose associated virtual open appointment waitlist data is consistent with the newly available healthcare service appointment; and automatically contacting the second healthcare service consumer using the second healthcare service consumer's mobile device contact information and sending the second healthcare service consumer data indicating the newly available healthcare service appointment and data indicating a designated period of time within which the second healthcare service consumer must accept the newly available healthcare service appointment.

* * * * *

UNITED STATES PATENT AND TRADEMARK OFFICE
CERTIFICATE OF CORRECTION

PATENT NO.        : 8,185,426 B1
APPLICATION NO.   : 12/263676
DATED             : May 22, 2012
INVENTOR(S)       : Siamak Khoubyari It is certified that error appears in the above-identified patent and that said Letters Patent is hereby corrected as shown below:

In the Claims

In Column 33, Line 46, Claim 1, before "each", insert --with--;
In Column 37, Line 49, Claim 10, between "associated" and "appointment", insert --with the newly available healthcare service appointment with the virtual open--;
In Column 38, Line 44, Claim 13, before "each", insert --with--;
In Column 39, Line 36, Claim 14, between "associated" and "each", insert --with--; and
In Column 40, Line 40, Claim 18, between "to" and "asso-", insert --determine a service consumer on the virtual open appointment waitlist whose--.

Signed and Sealed this
Twenty-fourth Day of June, 2014

Michelle K. Lee
*Deputy Director of the United States Patent and Trademark Office*